US011322256B2

(12) United States Patent
Sati et al.

(10) Patent No.: US 11,322,256 B2
(45) Date of Patent: May 3, 2022

(54) AUTOMATED LABELING OF IMAGES TO TRAIN MACHINE LEARNING

(71) Applicant: INTERNATIONAL BUSINESS MACHINES CORPORATION, Armonk, NY (US)

(72) Inventors: Marwan Sati, Mississauga (CA); David Richmond, Newton, MA (US)

(73) Assignee: International Business Machines Corporation, Armonk, NY (US)

( * ) Notice: Subject to any disclaimer, the term of this patent is extended or adjusted under 35 U.S.C. 154(b) by 653 days.

(21) Appl. No.: 16/205,224

(22) Filed: Nov. 30, 2018

(65) Prior Publication Data

US 2020/0176112 A1 Jun. 4, 2020

(51) Int. Cl.
*G06N 20/00* (2019.01)
*G16H 50/20* (2018.01)
(Continued)

(52) U.S. Cl.
CPC .............. *G16H 50/20* (2018.01); *G06F 40/30* (2020.01); *G06N 20/00* (2019.01); *G16H 15/00* (2018.01);
(Continued)

(58) Field of Classification Search
CPC ........ G06N 20/00; G16H 50/20; G16H 15/00; G16H 30/40; G06F 40/30; G06F 40/284;
(Continued)

(56) References Cited

U.S. PATENT DOCUMENTS

| 2005/0010445 A1* | 1/2005 | Krishnan | G06T 7/0012 705/2 |
| 2007/0165924 A1* | 7/2007 | Nicponski | G06T 7/0012 382/128 |

(Continued)

FOREIGN PATENT DOCUMENTS

| WO | 2017151757 A1 | 9/2017 | |
| WO | 2017151759 A1 | 9/2017 | |
| WO | WO-2017151757 A1 * | 9/2017 | ........... G06N 3/0454 |

OTHER PUBLICATIONS

Marinai et al., "Artificial Neural Networks for Document Analysis and Recognition," IEEE Transactions on Pattern Analysis and Machine Intelligence, Jan. 2005, p. 23-35, vol. 27, Issue 1.

(Continued)

*Primary Examiner* — Dave Misir
(74) *Attorney, Agent, or Firm* — Rakesh Roy (57) ABSTRACT

A method, computer system, and a computer program product for automatic labeling to train a machine learning algorithm is provided. The present invention may include labeling a medical image with at least one finding from a corresponding medical report. The present invention may include determining a localization information from the labeled medical image. The present invention may include training the machine learning algorithm with the determined localization information. The present invention may include detecting at least one candidate in a test medical image. The present invention may include generating a discrepancy list between the at least one detected candidate in the test medical image and at least one human-reported finding in a corresponding test medical report. The present invention may include, in response to determining that the generated discrepancy list is above a threshold, retraining the trained machine learning algorithm until the generated discrepancy list is below the threshold.

14 Claims, 6 Drawing Sheets

(51) Int. Cl.
  *G16H 15/00*    (2018.01)
  *G16H 30/40*    (2018.01)
  *G06F 40/30*    (2020.01)
  *G06F 40/205*   (2020.01)
  *G06F 40/284*   (2020.01)

(52) U.S. Cl.
  CPC ........... *G16H 30/40* (2018.01); *G06F 40/205* (2020.01); *G06F 40/284* (2020.01)

(58) Field of Classification Search
  CPC .............. G06F 40/205; G06F 17/2705; G06F 17/2785; G06F 17/277
  USPC .......................................................... 706/12
  See application file for complete search history.

(56) References Cited

U.S. PATENT DOCUMENTS

| | | | |
|---|---|---|---|
| 2009/0252394 A1 | 10/2009 | Liang et al. | |
| 2016/0364879 A1* | 12/2016 | Zankowski | G06T 7/11 |
| 2017/0221204 A1* | 8/2017 | Shinagawa | A61B 6/5217 |
| 2020/0286614 A1* | 9/2020 | Do | G16H 15/00 |
| 2021/0065859 A1* | 3/2021 | Mckinney | G16H 30/40 |

OTHER PUBLICATIONS

Mell et al., "The NIST Definition of Cloud Computing," National Institute of Standards and Technology, Sep. 2011, p. 1-3, Special Publication 800-145.

\* cited by examiner

AUTOMATED LABELING OF IMAGES TO TRAIN MACHINE LEARNING

BACKGROUND

The present invention relates generally to the field of computing, and more particularly to medical imaging.

Medical imaging studies of a patient are often conducted as part of diagnostic decision making and treatments. A doctor may typically analyze a medical image and generate a medical report including a written description of the observed findings and the anatomical location of the observed findings within the medical image. More recently, artificial intelligence (AI) techniques have been implemented to build machine learning models that can automatically analyze medical images.

SUMMARY

Embodiments of the present invention disclose a method, computer system, and a computer program product for automatic labeling to train a machine learning algorithm. The present invention may include labeling a medical image with at least one finding from a corresponding medical report. The present invention may include determining a localization information from the labeled medical image. The present invention may include training the machine learning algorithm with the determined localization information. The present invention may include detecting at least one candidate in a test medical image. The present invention may include generating a discrepancy list between the at least one detected candidate in the test medical image and at least one human-reported finding in a corresponding test medical report. The present invention may include, in response to determining that the generated discrepancy list is above a threshold, retraining the trained machine learning algorithm until the generated discrepancy list is below the threshold.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product for automatic labeling to train machine learning. As such, the present embodiment has the capacity to improve the technical field of medical imaging by automatically correlating medical report findings with potential findings or candidates in a corresponding medical image to help train a machine learning algorithm to detect target structures in medical images. More specifically, information from a medical report may be used to automatically associate a description of a finding in the medical report with one or more potential candidates in a medical image (e.g., potential candidates from output of a computer algorithm, AI). Natural language processing (NLP) may be used to automatically read the medical report and determine a location of the described finding within the corresponding medical image. The described finding may be automatically correlated to the associated candidate in the medical image and may be specifically annotated (e.g., electronically marked) as a strongly labeled finding in the medical image. The strongly labeled information may be fed into the machine learning algorithm to improve the quality of the training data and accelerate the machine learning for detecting target structures in subsequent medical images.

As described previously, medical imaging studies of a patient are often conducted as part of diagnostic decision making and treatments. A doctor may typically analyze a medical image and generate a medical report including a written description of the observed findings and the anatomical location of the observed findings within the medical image. More recently, AI techniques have been implemented to build machine learning models that can automatically analyze medical images.

For image-based machine learning, an algorithm may be trained using a set of labeled training data (e.g., labeled medical images) to detect diagnostically relevant target structures in new medical images. The medical images may be labeled with a description of the relevant medical findings (e.g., features) contained within each image (e.g., ground truth label) in order to help the algorithm understand the relevant medical findings of the relevant targets. Machine learning may be accelerated and improved by strongly labeled target structures (e.g., a cancer lesion) in the medical image. The target structure may be strongly labeled by annotating (e.g., electronically marking or labeling) the target structure within the medical image. The annotated target structure may be delineated within the medical image (e.g., via an outline) to help the algorithm understand what the target structure looks like within the medical image.

In many instances, a doctor may not electronically mark (e.g., strongly label) the observed findings (e.g., target structures) within a medical image. The medical image may be physically marked (e.g., with an arrow or circle) and may include a corresponding medical report with a natural language description of the findings and the anatomical locations of the findings observed by a doctor within the medical image. However, in such instances, the medical image may not include an electronic link between the target structure in the medical image and the observed findings described in the medical report.

There are existing methods to automatically read the medical report to understand the findings (e.g., cancer lesions) observed by the doctor in the medical image. Similarly, in such instances, the medical image may not be labeled with the observed findings in a manner suitable for training the algorithm to automatically detect the relevant target structures. There are Computer Aided Detection (CAD) methods that may identify suspected findings within a medical image (e.g., lung CAD). However, the clinical usefulness of CAD methods has been reduced due to known detection of too many false positive findings.

Therefore, it may be advantageous to, among other things, provide a way to automatically correlate medical report findings with medical image candidates to generate strongly labeled training data to quickly and efficiently train machine learning methods to detect relevant targets within medical images.

According to at least one embodiment, a cognitive imaging program may implement natural language processing (NLP) to read a medical report and automatically detect findings (e.g., lesions, tumors, diseases) and the anatomical location of the findings reported by a doctor. The cognitive imaging program may also implement an image detection component (e.g., image detection algorithm) to automatically detect potential findings within the medical image and to automatically detect the anatomy within the medical image. Then, the cognitive imaging program may implement an algorithm which may automatically associate the findings from the medical report with the potential findings from the medical image based on a description of the location of the finding in the report and the anatomical location of the potential finding in the medical image. Thereafter, the cognitive imaging program may record the association of the findings from the medical report and the potential findings from the medical image as strongly labeled information. The cognitive imaging program may then feed the strongly labeled information into a machine learning algorithm to help train the machine learning algorithm to automatically detect the target structure.

According to at least one embodiment, once the machine learning algorithm starts to detect target structures within the medical images, the cognitive imaging program may implement the machine learning algorithm to automatically label target structures in new training studies. The machine learning algorithm may be used to replace the image detection algorithm (e.g., CAD) once the machine learning algorithm reaches a similar detection performance. Importantly, the sensitivity of the machine learning algorithm may be controlled through a detection threshold (e.g., confidence score). Initially, the machine learning algorithm may have a high false positive detection rate, similar to the image detection algorithm. However, as the machine learning algorithm improves, the detection threshold may be safely increased, thereby reducing the number of false positive detections. The detection threshold of the machine learning algorithm may be tuned to gradually improve the quality of the ground truth labeling, and thereby may be used to improve the performance of the machine learning algorithm.

According to at least one embodiment, the image detection component may be the machine learning algorithm being trained through the labeling process. As such, the machine learning algorithm may essentially train itself using an iterative learning method. The machine learning algorithm may be given a set of medical reports and associated medical images. The machine learning algorithm may automatically read the medical reports and may automatically weakly label the associated medical images with one or more potential findings (e.g., lung cancer). After a certain number of medical reports and associated medical images are ingested, the machine learning algorithm may try and detect potential findings (e.g., cancer lesions) in previously unseen medical images. Then, the machine learning algorithm may compare the potential findings from the medical image with what the doctor described in the medical report. A discrepancy list may be established between the machine-found findings and the human-reported findings. The machine learning algorithm may continue to analyze more medical images and read more medical reports until the discrepancy list is below a threshold set by a human user. In one embodiment, the threshold may include the accuracy that the doctor may have at detecting lung cancer.

Figure 1:
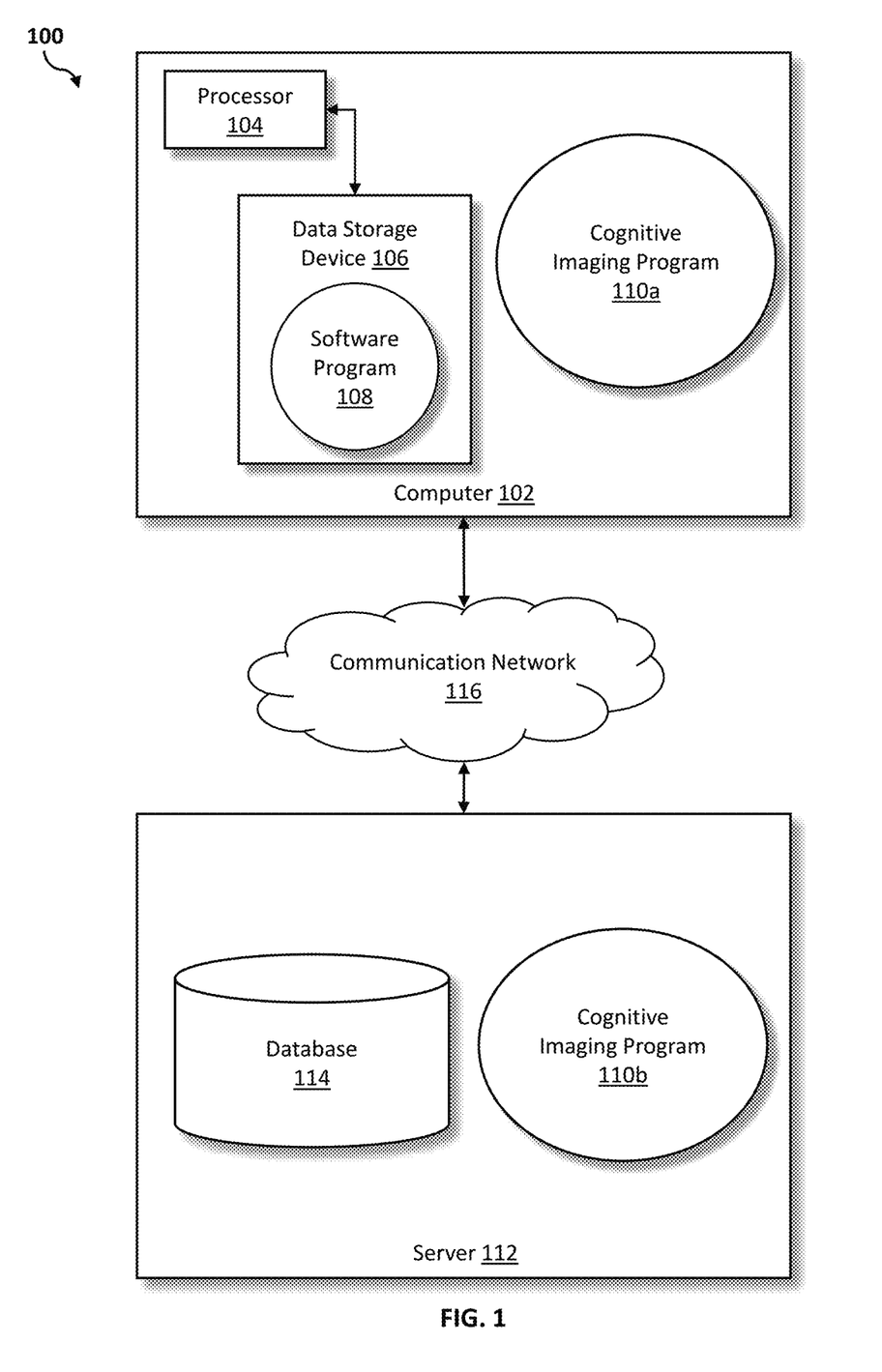
FIG. 1 illustrates a networked computer environment according to at least one embodiment.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a cognitive imaging program 110*a*. The networked computer environment 100 may also include a server 112 that is enabled to run a cognitive imaging program 110*b* that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 4, server computer 112 may include internal components 902*a* and external components 904*a*, respectively, and client computer 102 may include internal components 902*b* and external components 904*b*, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the cognitive imaging program 110*a*, 110*b* may interact with a database 114 that may be embedded in various storage devices, such as, but not limited to a computer/mobile device 102, a networked server 112, or a cloud storage service.

According to the present embodiment, a user using a client computer 102 or a server computer 112 may use the cognitive imaging program 110*a*, 110*b* (respectively) to automatically associate detected findings from a medical report with detected candidates from a medical image to generate a labeled training data to quickly and efficiently train machine learning methods to detect target structures within medical images. The cognitive imaging method is explained in more detail below with respect to FIGS. 2 and 3.

Figure 2:
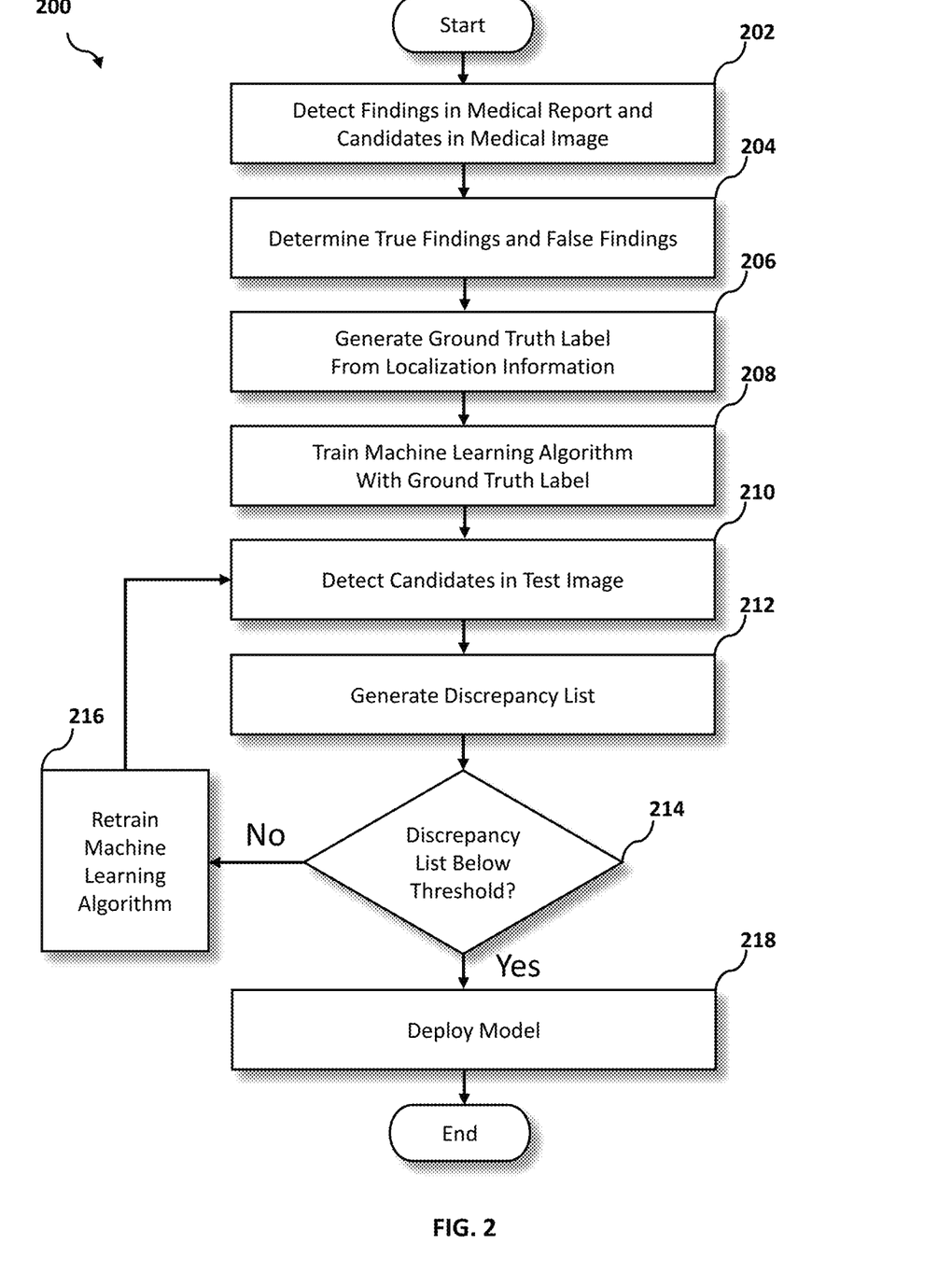
FIG. 2 is an operational flowchart illustrating a process for cognitive imaging according to at least one embodiment.

Referring now to FIG. 2, an operational flowchart illustrating the exemplary cognitive imaging process 200 used by the cognitive imaging program 110a, 110b according to at least one embodiment is depicted.

At 202, one or more findings are detected in a medical report and one or more candidates are detected in a corresponding medical image. Detecting may include sensing, receiving, discovering, acquiring, or recognizing. The cognitive imaging program 110a, 110b running on a user device (e.g., client computer 102 or server computer 112) may receive (e.g., via communication network 116) a first or unlabeled dataset including one or more medical reports and one or more corresponding medical images from a corpus stored in the database 114.

The medical images may depict the internal bodily organs and structures of a patient and may be acquired using known medical imaging techniques such as, computed tomography (CT), magnetic resonance imaging (MRI), and ultrasound. The medical images may include two-dimensional and/or three-dimensional images. The medical reports may include written medical interpretations (e.g., text document) of the corresponding medical images. The medical reports may include informationally rich, structured content, such as natural language descriptions of observations or findings made by doctors or other subject matter experts analyzing the corresponding medical images (e.g., a radiologist analyzing a medical image and detecting lung cancer). In one embodiment, the medical reports may also include natural language descriptions of the anatomical locations of the findings observed within the corresponding medical images. In one embodiment, the medical reports may include a radiology report interpreting the corresponding medical images. In at least one embodiment, the medical reports may also include pathology report containing a diagnosis based on cells and tissue analysis. According to another embodiment, the medical reports may include any other suitable diagnostic reports.

In order to generate a model which may accurately detect a target structure in a medical image (e.g., finding reported in a corresponding medical report), a machine learning algorithm may need a labeled training dataset including training images labeled with a description of what is contained within each training image in order to help the machine learning algorithm learn what the target structure looks like (e.g., lung with cancer). However, the medical images in the unlabeled dataset may not initially include the requisite labels linking the medical images to the findings in the corresponding medical reports. Accordingly, the cognitive imaging program 110a, 110b may first process the unlabeled dataset in order to provide the labeled training data for subsequent use by the machine learning algorithm.

In response to receiving the medical report from the unlabeled dataset, the cognitive imaging program 110a, 110b may implement a natural language processing (NLP) component or algorithm to determine one or more report data. Specifically, the NLP algorithm may breakdown and analyze the text of the medical report using existing NLP methods (e.g., sentence segmentation, tokenization, parts-of-speech tagging, parsing, fact extraction). Then, the NLP algorithm may process the textual data in the medical report and may automatically detect the findings (e.g., lesions, nodules, diseases, tumors, fractures) and the geometric description of the anatomical location (e.g., left lung, superior lobe) of the findings observed by the doctor. The report data may include the findings and the anatomical location of the findings detected using the NLP algorithm of the cognitive imaging program 110a, 110b.

In response to receiving the corresponding medical image from the unlabeled dataset, the cognitive imaging program 110a, 110b may determine image data from the medical image. Specifically, the cognitive imaging program 110a, 110b may implement an image detection component (e.g., image detection algorithm) to automatically detect one or more potential findings or candidates (e.g., lesions, nodules, diseases, tumors, fractures) within the medical image. In one embodiment, the image detection algorithm may include CAD detection methods. In at least one embodiment, the image detection algorithm may include AI detection methods.

The image detection algorithm may also automatically detect the anatomy depicted within the medical image. In one embodiment, the image detection algorithm may provide an anatomical map location (e.g., left lung, superior lobe) of each of the candidates detected in the medical image. The image detection algorithm for detecting the anatomy may implement the Atlas Label Fusion method. In another embodiment, the cognitive imaging program 110a, 110b may implement an anatomy detection component or algorithm or any suitable AI detection methods. In at least one embodiment, the cognitive imaging program 110a, 110b may implement the same image detection algorithm for detecting the candidates and the anatomical location of the candidates within the medical image. The resulting image data may include a candidate list containing one or more candidates detected in the medical image and the associated anatomical location of each detected candidate.

For example, the cognitive imaging program 110a, 110b running in a hospital server receives a medical report and a corresponding medical image from an unlabeled dataset stored in a corpus of the database 114. The medical image is an ultrasound medical image of a patient's kidneys acquired using existing ultrasound techniques.

The cognitive imaging program 110a, 110b implements an NLP algorithm to automatically analyze the text of the medical report and determine the report data. The NLP algorithm interprets the radiology observations made by the doctor from the ultrasound medical image and detects, from the text of the medical report, a finding of a tumor in the left kidney. In addition, the NLP algorithm interprets the pathology observations made by the doctor from a biopsy of kidney tissue and detects, from the text of the medical report, that the tumor in the left kidney is carcinoma. The cognitive imaging program 110a, 110b also implements an image detection algorithm to analyze the ultrasound medical image and determine the image data. The image detection algorithm implements AI detection methods and detects three suspicious lesions (three candidates; C1, C2, C3) in the ultrasound medical image. Further, the image detection algorithm detects the right kidney as the anatomical location of candidates C1, C2 and detects the left kidney as the anatomical location of candidate C3. The cognitive imaging program 110a, 110b generates a candidate list including the three candidate lesions C1, C2, C3 and the respective anatomical locations thereof.

Then, at 204, the true findings and the false findings are determined. Determining may include ascertaining, resolving, evaluating, formulating, computing, calculating, or comparing. Initially, the image detection algorithm may provide a lower quality assessment (e.g., too many false positive candidates) of the medical image at 202 as compared to the higher quality assessment of the medical image reported by the doctor in the corresponding medical report. As such, the image detection algorithm may include one or more candidates in the candidate list that may be false findings (e.g., false positive candidates). In order to accurately label the medical image with the findings reported by the doctor in the medical report, the cognitive imaging program 110a, 110b may compare the report data (e.g., findings detected by the NLP algorithm) against the image data (e.g., candidates in the candidate list detected by the image detection algorithm).

The cognitive imaging program 110a, 110b may determine the one or more true findings and the one or more false findings by associating the findings from the medical report with the candidate list detected from the medical image. In one embodiment, the cognitive imaging program 110a, 110b may include an association algorithm. The association algorithm may receive the image data including the candidates detected by the image detection algorithm and the report data including the findings detected by the NLP algorithm. The association algorithm may interpret the geometric description of the anatomical location of the finding in the medical report and may identify the corresponding candidate in the medical image based on the detected anatomical location (e.g., via the image detection algorithm) of the candidate in the medical image. Using this process, the association algorithm may map a candidate or subset of candidates from the medical image to the finding from the medical report and may return the one or more mapped candidates as the true finding. In one embodiment, the association algorithm may determine a localization information (e.g., location of the true finding in a sub-region of the medical image) of the true finding from the medical report.

Continuing with the previous example, the association algorithm receives the ultrasound medical image of the kidneys including the three candidate lesions C1, C2, C3 and the corresponding medical report including the finding of the tumor in the left kidney. The association algorithm interprets the geometric description of the finding in the medical report and determines the anatomical location of the tumor to be in the left kidney. Thereafter, the association algorithm maps candidate lesion C3 (detected in the left kidney) from the medical image to the finding from the medical report and returns candidate lesion C3 as the true finding.

Then, at 206, a ground truth label is generated from the localization information. The cognitive imaging program 110a, 110b may generate (e.g., create, establish, compile, structure, construct, assemble, form, organize, provide, introduce) the ground truth label from the localization information. The cognitive imaging program 110a, 110b may convert one or more medical images from the unlabeled dataset into labeled training data by electronically linking the medical images of the unlabeled dataset with ground truth labels from corresponding medical reports. A ground truth label may be associated with a medical image in order to provide an objective (e.g., the correct answer) when training a machine learning algorithm to detect the target structure (e.g., the objective; lesions, cancer) in the medical image. During the training process, one or more parameters (e.g., weights) of the machine learning algorithm may be modified based on the relationship between the medical image and the associated ground truth label to enable the machine learning algorithm to detect (e.g., predict) the target structure in the medical image.

In one embodiment, the findings in the medical report may provide a ground truth associated with the corresponding medical image. The cognitive imaging program 110a, 110b may implement a labeling component to generate the ground truth labeling for the medical image based on the ground truth provided in the corresponding medical report. The labeling component may annotate the true finding in the medical image based on the localization information of the true finding provided by the association algorithm. In one embodiment, the labeling component may annotate the medical image by electronically marking one or more pixels in the medical image (e.g., based on the localization information) indicating or delineating the contour or features of the true finding in the medical image (e.g., localized true finding). Then, the labeling component may electronically label the localized true finding with the associated finding (e.g., ground truth) from the medical report. In one embodiment, an electronic label of the localized true finding may include report data from the radiology report (e.g., tumor in left kidney) and report data from an associated pathology report (e.g., tumor is carcinoma). Thereafter, the labeling component may use the strongly labeled information (e.g., combination of the localized true finding and the associated label from the medical report) to generate the ground truth label for the medical image. The ground truth label may provide a localized electronic description (e.g., at the pixel level) of the target structure to enable modifications of the machine learning algorithm parameters to quickly and accurately converge on the target structure in the medical image.

Continuing with the previous example, the labeling component annotates the true finding in the ultrasound medical image by electronically marking the pixels delineating the contour of candidate lesion C3. Thereafter, the labeling component associates the ground truth from the medical report (radiology report and pathology report) with candidate lesion C3 and generates a ground truth label indicating that lesion C3 is a carcinoma tumor.

Then, at 208, the machine learning algorithm is trained with the ground truth label. After processing the unlabeled dataset into the labeled training data, the cognitive imaging program 110a, 110b may feed the labeled training data, including training images and the associated ground truth labels, into the machine learning algorithm. Thereafter, the machine learning algorithm may build a model which may accurately detect the target structure (e.g., as indicated by the ground truth label) in the training images of the labeled training data.

The machine learning algorithm may generate the model by iterating through a corrective or positive feedback loop. Specifically, the machine learning algorithm may detect (e.g., predict) one or more candidates in the training image. Then, the machine learning algorithm may compare the predicted candidates against the ground truth label to calculate an error. Thereafter, the machine learning algorithm may modify or adjust its parameters in order to decrease the error or difference between the predicted candidates and the ground truth label.

The performance of the machine learning algorithm may be further improved by improving the quality of the ground truth labels being fed into the machine learning algorithm. Once the machine learning algorithm is able to detect candidates in the training images at a rate similar to the initial image detection algorithm (e.g., CAD) at 202, the cognitive imaging program 110a, 110b may replace the image detection algorithm with the machine learning algorithm at 202 for processing the medical images in the unlabeled dataset. Specifically, the cognitive imaging program 110a, 110b may implement the machine learning algorithm to detect candidates in the medical images of the unlabeled dataset which may then be associated with the findings detected in the corresponding medical reports for generating ground truth labels.

In one embodiment, the cognitive imaging program 110a, 110b may control the detection sensitivity of the machine learning algorithm using a detection threshold. The detection threshold may be tuned to instruct the machine learning algorithm to only return candidates that meet or exceed a confidence score (e.g., 0.5 confidence that the candidate may include the target structure). Initially, the cognitive imaging program 110a, 110b may set a low detection threshold (e.g., 0.1 confidence) so that the machine learning algorithm may return a large number of candidates. Although the low detection threshold may return several false positive candidates in the large candidate list, the large candidate list may ensure that the findings detected in the medical report may be mapped to at least one candidate in the candidate list to determine the true finding in the candidate list. As the performance of the machine learning algorithm improves through training at 208, the cognitive imaging program 110a, 110b may gradually increase the detection threshold so that the machine learning algorithm may only return candidates with high confidence scores (e.g., 0.7 confidence), thereby reducing the number of false positive findings in the candidate list. Using this approach, the cognitive imaging program 110a, 110b may associate only high-quality candidates from the medical image back to the findings in the medical report, thereby increasing the quality of the true findings and improving the quality of the ground truth labels in the training images of the labeled training data. In at least one embodiment, the cognitive imaging program 110a, 110b may provide the user (e.g., a doctor, subject matter expert, any suitable human user) with an option to set the detection threshold to control the detection sensitivity of the machine learning algorithm.

Continuing with the previous example, the cognitive imaging program 110a, 110b feeds the labeled training data, including training images and the associated ground truth labels, into the machine learning algorithm. Once the machine learning algorithm starts to detect candidates within the training images, the cognitive imaging program 110a, 110b replaces the image detection algorithm with the machine learning algorithm to process new medical images for ground truth labeling. Initially, the cognitive imaging program 110a, 110b sets a low detection threshold which instructs the machine learning algorithm to return candidates above a 0.1 confidence score. However, as the performance of the machine learning improves through training at 208, the cognitive imaging program 110a, 110b sets a high detection threshold which instructs the machine learning algorithm to return candidates above a 0.8 confidence score. As a result, the machine learning algorithm returns higher quality candidate lists which are then mapped to the findings in the corresponding medical reports to generate high-quality ground truth labels for the labeled training data.

Then, at 210, one or more candidates are detected in a test image. After training the machine learning algorithm using the labeled training data, the cognitive imaging program 110a, 110b may evaluate or test the performance of the model using a test dataset (e.g., subset of the unlabeled dataset). The test dataset may include test medical reports and test medical images which have not been seen by the machine learning algorithm. In response to receiving the test medical image, the cognitive imaging program 110a, 110b may implement the model to detect (e.g., predict) one or more candidates in the test medical image.

Continuing with the previous example, after training the machine learning algorithm using the labeled training data, the cognitive imaging program 110a, 110b feeds the machine learning algorithm with a test medical image including a new (previously not seen) ultrasound medical image of a patient's kidneys. In response to receiving the test medical image, the machine learning algorithm returns a prediction, detecting four candidate lesions L1, L2, L3, L4 in the right kidney depicted in the test medical image.

Then, at 212, a discrepancy list is generated. The cognitive imaging program 110a, 110b may automatically compare the predicted candidates detected by the machine learning algorithm in the test medical image against the findings (e.g., ground truth) in the corresponding test medical report to determine the performance of the model. In one embodiment, the cognitive imaging program 110a, 110b may implement the NLP algorithm to analyze the test medical report and detect the findings therein. The cognitive imaging program 110a, 110b may establish the discrepancy list between the machine-detected findings (e.g., candidates detected by the machine learning algorithm) and the human-reported findings (e.g., ground truth; observed by the doctor) to determine the false findings (e.g., false positive candidates) detected by the machine learning algorithm.

Continuing with the previous example, the cognitive imaging program 110a, 110b implements the NLP algorithm to analyze the corresponding test medical report. From the test medical report, the cognitive imaging program 110a, 110b determines that the doctor observed two tumors T1, T2 in the right kidney. Based on the geometric descriptions of the two tumors T1, T2, the cognitive imaging program 110a, 110b maps the two tumors T1, T2 to candidate lesions L1, L4 detected by the machine learning algorithm in the corresponding test medical image. Thereafter, the cognitive imaging program 110a, 110b establishes the discrepancy list including candidate lesions L2, L3 which were not mapped to the findings in the corresponding test medical report.

Then, at 214, an inquiry is made to determine if the discrepancy list is below a threshold. The cognitive imaging program 110a, 110b may provide the user (e.g., a doctor, subject matter expert, any suitable human user) with an option to set a threshold as a performance measure for the model. In one embodiment, the threshold may be set to the accuracy of a doctor when detecting a target structure in a medical image (e.g., accuracy of detecting lung cancer).

Continuing with the previous example, the cognitive imaging program 110a, 110b provides the user with the option to set a threshold to measure the performance of the model. In response, the user sets the threshold to 10% inaccuracy—the 90% accuracy of a radiologist at detecting kidney cancer based on an ultrasound medical image. Accordingly, the cognitive imaging program 110a, 110b determines if the discrepancy list, including false positive candidates L2, L3, is below the 10% inaccuracy threshold set by the user.

If the cognitive imaging program 110a, 110b determines that the discrepancy list is not below the threshold at 214, then the machine learning algorithm is retrained at 216. In one embodiment, the cognitive imaging program 110a, 110b may feed the discrepancy list, including the false positive candidates detected in the test medical images, back into the machine learning algorithm. The machine learning algorithm may use the false positive candidates and the ground truths automatically detected from the findings in the corresponding test medical reports to calculate the error. Thereafter, the machine learning algorithm may use the calculated error to adjust or refine its parameters. In one embodiment, the cognitive imaging program 110a, 110b may retrain the machine learning algorithm using additional labeled training data until the discrepancy list is below the threshold set by the user.

Continuing with the previous example, based on the discrepancy list, including false positive candidates L2, L3, the cognitive imaging program 110a, 110b determines that the 50% inaccuracy of the machine learning algorithm is not below the 10% inaccuracy threshold set by the user at 214. Accordingly, the cognitive imaging program 110a, 110b feeds the discrepancy list and the ground truths automatically detected from the findings in the corresponding test medical report back into the machine learning algorithm in order to retrain the machine learning algorithm at 216. Thereafter, the cognitive imaging program 110a, 110b retrains the machine learning algorithm using additional labeled training data until the discrepancy list meets or is below the 10% inaccuracy threshold set by the user.

However, if the cognitive imaging program 110a, 110b determines that the discrepancy list meets or is below the threshold at 214, then the model is deployed at 218. Once the machine learning algorithm is capable of detecting the target structure in the test medical images with an accuracy that meets or is below the inaccuracy threshold set by the user, the cognitive imaging program 110a, 110b may deploy the model to detect the target structures in new, future datasets.

Continuing with the previous example, if the cognitive imaging program 110a, 110b determines that there is no discrepancy between the candidates detected by the machine learning algorithm in the test medical image and the findings described in the corresponding test medical report at 212, the cognitive imaging program 110a, 110b determines that the performance of the model (e.g., 0% inaccuracy) meets or is below the 10% inaccuracy threshold set by the user at 214. Accordingly, the cognitive imaging program 110a, 110b deploys the model to detect the target structures in new, future datasets at 218.

Figure 3:
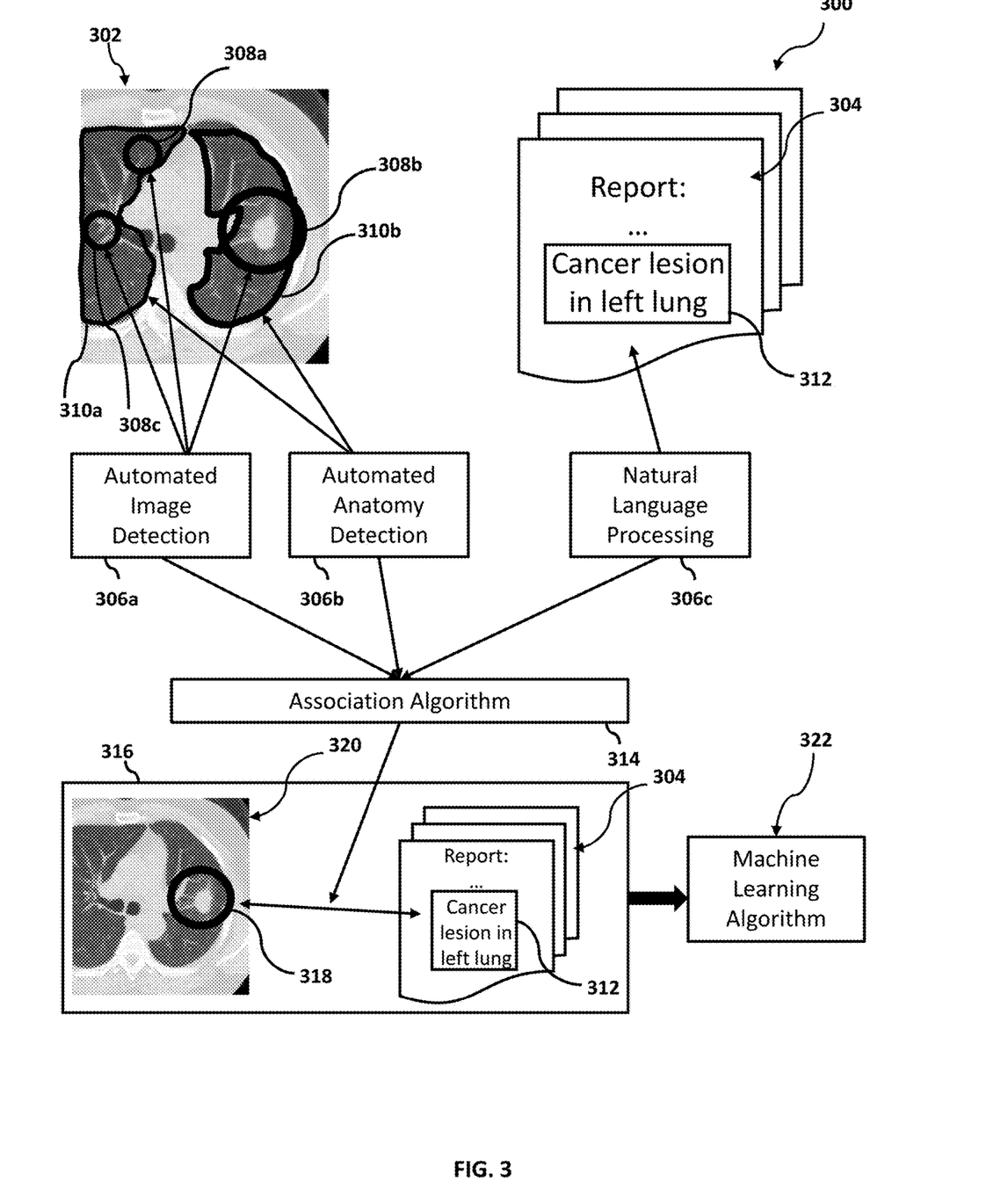
FIG. 3 is a block diagram illustrating an exemplary automated labeling process according to at least one embodiment.

Referring now to FIG. 3, an exemplary illustration of an automated labeling process 300 according to at least one embodiment is depicted. The cognitive imaging program 110a, 110b receives a medical image 302 and a corresponding medical report 304 from an unlabeled dataset (e.g., stored in a hospital network), as previously described at 202. Initially there are no electronic links between the medical image 302 and the corresponding medical report 304. The cognitive imaging program 110a, 110b implements an image detection component 306a and automatically detects or identifies three candidate lesions 308a, 308b, 308c in the medical image 302, as previously described at 202. Further, the cognitive imaging program 110a, 110b implements an anatomy detection component 306b and automatically identifies or detects a right lung 310a and a left lung 310b depicted in the medical image 302, as previously described at 202. The cognitive imaging program 110a, 110b also implements a natural language processing component 306c to read the medical report 304. Based on the analysis of the medical report 304 by the natural language processing component 306c, the cognitive imaging program 110a, 110b detects a finding 312, indicating that a doctor observed a cancer lesion in the left lung, as previously described at 202.

Then, the output of the image detection component 306a, the anatomy detection component 306b, and the natural language processing component 306c are fed into an association algorithm 314, as previously described at 204. The association algorithm 314 interprets the geometric description of the anatomical location of the finding 312. Then, the association algorithm 314 maps the finding 312 to the candidate list provided by the image detection component 306a based on the anatomical locations provided by the anatomy detection component 306b. As a result, the association algorithm 314 maps the finding 312 to the candidate lesion 308b detected in the left lung 310b, as previously described at 204. Accordingly, the candidate lesion 308b is determined to be a true finding based on the ground truth provided by the finding 312 in the medical report 304, as previously described at 204.

Then, the output of the association algorithm 314 is fed into a labeling component 316 of the cognitive imaging program 110a, 110b, as previously described at 206. Based on the determination that the candidate lesion 308b is the true finding, the labeling component 316 generates a ground truth label 318 for the candidate lesion 308b, as previously described at 206. The ground truth label 318 electronically marks the pixels of the candidate lesion 308b and labels the electronically marked pixels as a cancer lesion in the left lung, by association with the finding 312 in the medical report 304, as previously described at 206. By generating the ground truth label 318, the labeling component 316 converts the medical image 302 into a labeled training data 320, as previously described at 206. Thereafter, the cognitive imaging program 110a, 110b feeds the labeled training data 320 into a machine learning algorithm 322 in order to train the machine learning algorithm 322 to detect a target structure indicated by the ground truth label 318, as previously described at 208.

One other embodiment may include a self-training machine learning algorithm configured to detect the target structures in medical images without an advanced starting point or helper algorithm such as the image detection algorithm (e.g., CAD) at 202. The machine learning algorithm may receive and ingest a set of unlabeled medical images and corresponding medical reports from an unlabeled dataset. In one embodiment, the machine learning algorithm may analyze the medical reports and analyze the corresponding unlabeled medical images to learn a high level (e.g., image level) view of what is contained within the unlabeled medical images. Specifically, the machine learning algorithm may read (e.g., via NLP algorithm) a medical report and automatically generate a weak label for a corresponding unlabeled medical image based on at least one finding detected from the medical report (e.g., lung cancer). It is contemplated that after ingesting a certain number (e.g., 10,000) of medical reports and the corresponding weakly labeled medical images, the machine learning algorithm may generate a localization information associated with the findings in the medical report. Thereafter, the machine learning algorithm may try to detect candidates in new test images, previously not seen by the machine learning algorithm. In one embodiment, the machine learning algorithm may detect candidates in a test image and automatically compare the detected candidates against the findings reported by a doctor in the corresponding test report. The machine learning algorithm may associate the findings from the test report with the list of detected candidates from the test image to determine the true findings (e.g., true positive candidates) and the false findings (e.g., false positive candidates). Thereafter, the true findings may be fed back into the machine learning algorithm as positive feedback and the false findings may be fed back into the machine learning algorithm as negative feedback. The machine learning algorithm may iteratively train using the positive feedback and the negative feedback until the number of false positive candidates detected by the machine learning algorithm is below a threshold set by a user.

As described herein, machine learning methods for detecting target structures in medical images may require a large sample of labeled training data. Labeled training data may be prepared by subject matter experts, such as radiologists, who may annotate each medical image with one or more ground truth labels indicating the expert observed findings therein. Due to the large number of labeled training data required for training machine learning methods, the typical process of labeling medical images may be time and cost prohibitive.

Accordingly, the cognitive imaging program 110a, 110b described herein may help train machine learning methods more quickly, efficiently, and cost effectively by automatically labeling candidates detected in medical images with findings detected in associated medical reports. The cognitive imaging program 110a, 110b may interpret a medical report using an NLP algorithm and determine the anatomical location of a finding observed in a corresponding medical image. The cognitive imaging program 110a, 110b may map the finding from the medical report to a candidate detected in the corresponding medical image using an image detection algorithm. Thereafter, the cognitive imaging program 110a, 110b may generate a ground truth label for the detected candidate and feed the labeled training data into a machine learning algorithm. Thus, the cognitive imaging program 110a, 110b may improve the quality of the training data to help accelerate machine learning and improve the functionality of a computer.

It may be appreciated that FIGS. 2 and 3 provide only an illustration of one embodiment and do not imply any limitations with regard to how different embodiments may be implemented. Many modifications to the depicted embodiment(s) may be made based on design and implementation requirements.

Figure 4:
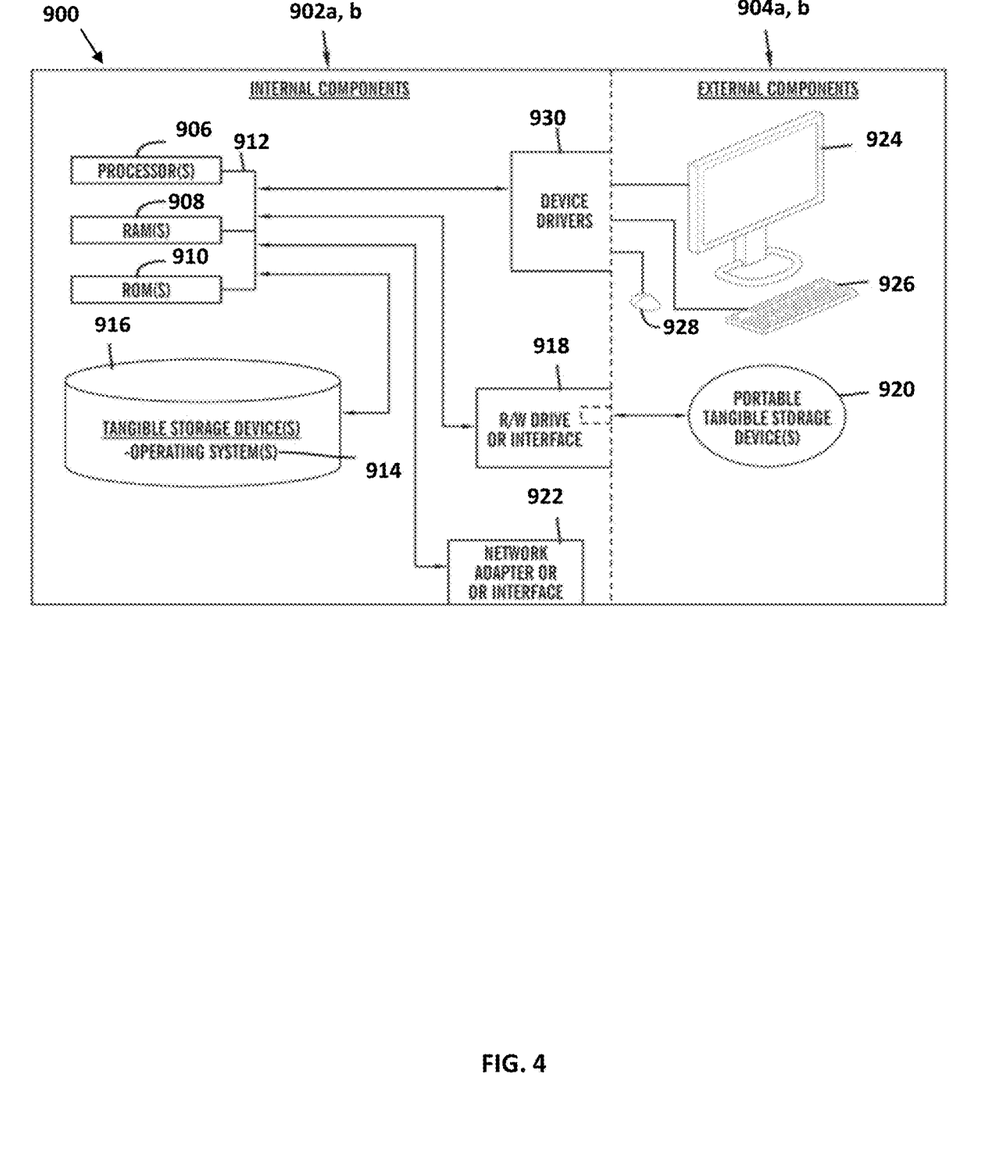
FIG. 4 is a block diagram of internal and external components of computers and servers depicted in FIG. 1 according to at least one embodiment.

FIG. 4 is a block diagram 900 of internal and external components of computers depicted in FIG. 1 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902a, b and external components 904a, b illustrated in FIG. 4. Each of the sets of internal components 902a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the cognitive imaging program 110a in client computer 102, and the cognitive imaging program 110b in network server 112, may be stored on one or more computer-readable tangible storage devices 916 for execution by one or more processors 906 via one or more RAMs 908 (which typically include cache memory). In the embodiment illustrated in FIG. 4, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the cognitive imaging program 110a and 110b can be stored on one or more of the respective portable computer-readable tangible storage devices 920, read via the respective R/W drive or interface 918 and loaded into the respective hard drive 916.

Each set of internal components 902a, b may also include network adapters (or switch port cards) or interfaces 922 such as a TCP/IP adapter cards, wireless wi-fi interface cards, or 3G or 4G wireless interface cards or other wired or wireless communication links. The software program 108 and the cognitive imaging program 110a in client computer 102 and the cognitive imaging program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the cognitive imaging program 110a in client computer 102 and the cognitive imaging program 110b in network server computer 112 are loaded into the respective hard drive 916. The network may comprise copper wires, optical fibers, wireless transmission, routers, firewalls, switches, gateway computers and/or edge servers.

Each of the sets of external components 904a, b can include a computer display monitor 924, a keyboard 926, and a computer mouse 928. External components 904a, b can also include touch screens, virtual keyboards, touch pads, pointing devices, and other human interface devices. Each of the sets of internal components 902a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
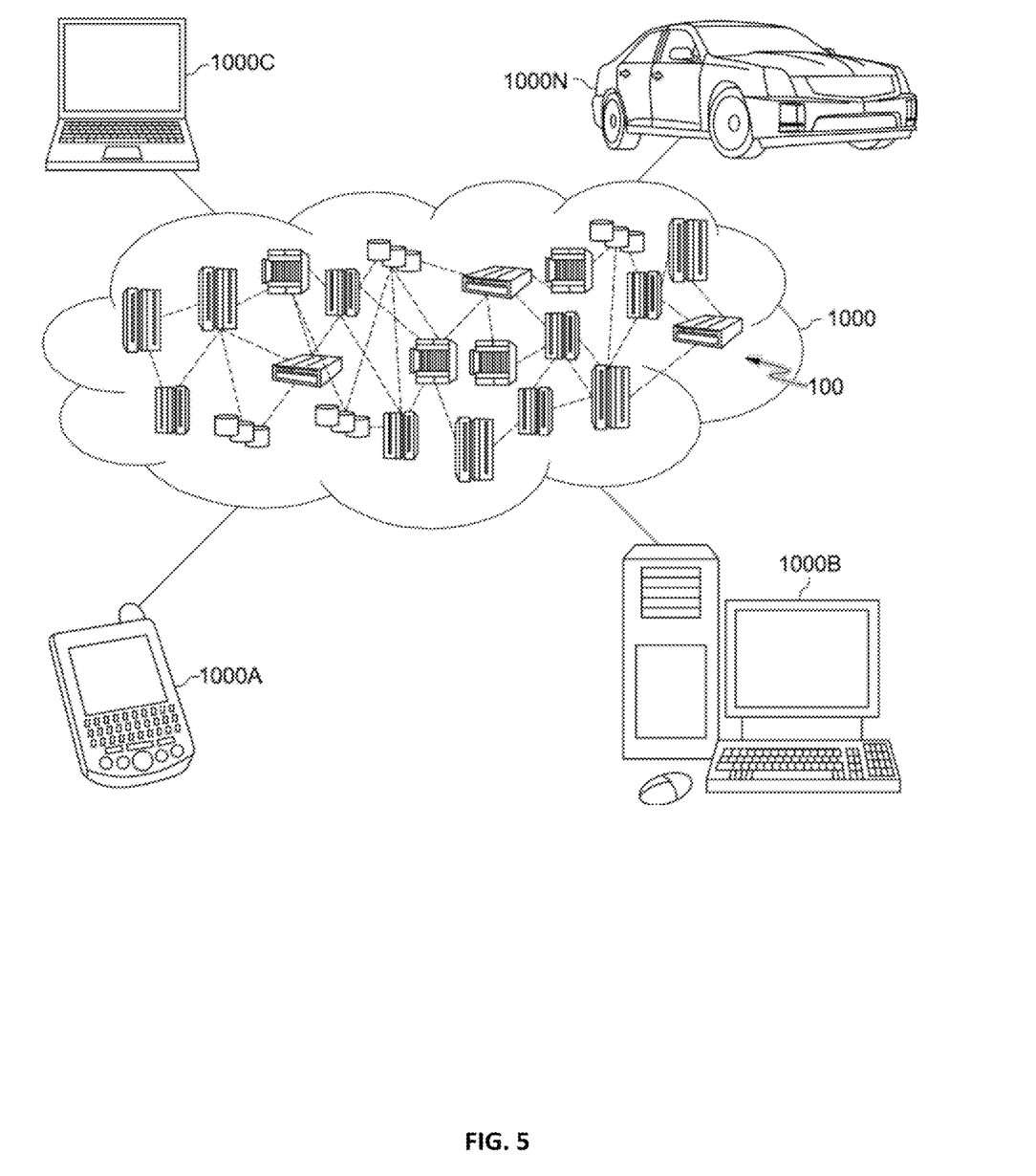
FIG. 5 is a block diagram of an illustrative cloud computing environment including the computer system depicted in FIG. 1, in accordance with an embodiment of the present disclosure.

Referring now to FIG. 5, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 5 are intended to be illustrative only and that computing nodes 100 and cloud computing environment 1000 can communicate with any type of computerized device over any type of network and/or network addressable connection (e.g., using a web browser).

Figure 6:
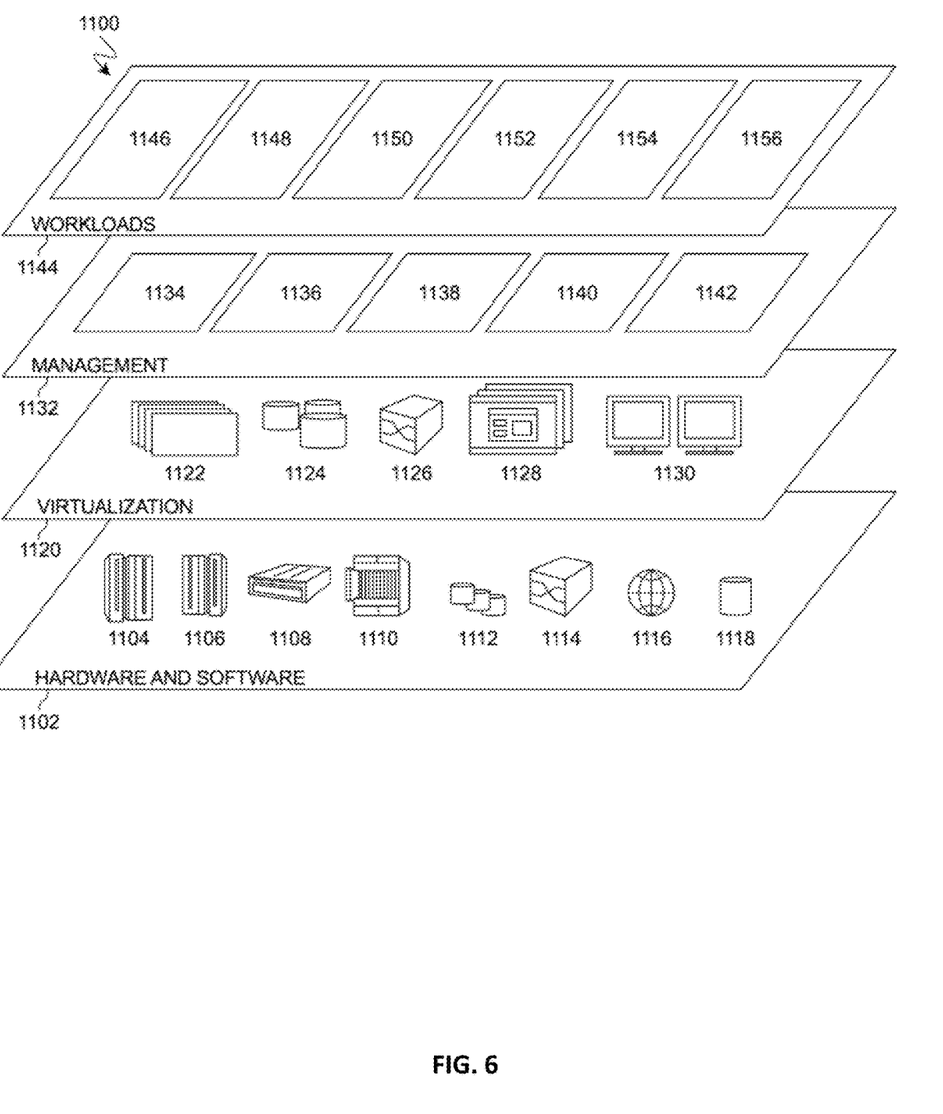
FIG. 6 is a block diagram of functional layers of the illustrative cloud computing environment of FIG. 5, in accordance with an embodiment of the present disclosure.

Referring now to FIG. 6, a set of functional abstraction layers 1100 provided by cloud computing environment 1000 is shown. It should be understood in advance that the components, layers, and functions shown in FIG. 6 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and cognitive imaging 1156. A cognitive imaging program 110a, 110b provides a way to automatically correlate medical report findings with potential findings or candidates in a corresponding medical image to generate labeled training data to help train a machine learning algorithm to detect target structures in medical images.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for automatic labeling to train a machine learning algorithm, the method comprising:
    detecting at least one first finding in a medical report and at least one first candidate in a corresponding medical image;
    interpreting a geometric description of an anatomical location of the detected at least one first finding in the medical report;
    identifying, using an association algorithm, at least one true finding from the detected at least one first candidate in the corresponding medical image based on the interpreted geometric description of the anatomical location of the detected at least one finding in the medical report;
    locating, in a sub-region of the corresponding medical image, the detected at least one first candidate based on the interpreted geometric description of the anatomical location of the detected at least one first finding in the medical report;
    electronically marking the located at least one first candidate in the sub-region of the corresponding medical image;
    generating a ground truth label by labeling, in a natural language, the electronically marked at least one first candidate in the sub-region of the corresponding medical image with the detected at least one first finding in the medical report;
    training the machine learning algorithm with the generated ground truth label;
    detecting, using the trained machine learning algorithm, at least one second candidate in a test medical image, wherein the at least one detected second candidate in the test medical image is associated with predicting at least one second finding from a corresponding test medical report;
    generating, using the trained machine learning algorithm, a discrepancy list between the at least one detected second candidate in the test medical image and the at least one second finding in the corresponding test medical report; and
    in response to determining that the generated discrepancy list is above a threshold, retraining the trained machine learning algorithm until the generated discrepancy list is below the threshold.

2. The method of claim 1, further comprising:
    determining at least one true finding from the detected at least one first candidate in the corresponding medical image, by association with the detected at least one first finding from the medical report.

3. The method of claim 1, further comprising:
    determining a ground truth in the detected at least one first finding from the medical report; and
    generating the ground truth label for the identified at least one true finding in the corresponding medical image based on the determined ground truth from the medical report.

4. The method of claim 3, wherein generating the ground truth label for the identified at least one true finding in the corresponding medical image further comprises:
    electronically marking, using a labeling component, at least one pixel indicating a contour of the identified at least one true finding in the corresponding medical image.

5. The method of claim 3, wherein generating the ground truth label for the identified at least one true finding in the corresponding medical image further comprises:
    providing an electronic label associated with at least one medical report data, wherein the at least one medical report data is selected from the group consisting of: at least one radiology report data and at least one pathology report data.

6. A computer system for automatic labeling to train a machine learning algorithm, comprising:
    one or more processors, one or more computer-readable memories, one or more computer-readable tangible storage media, and program instructions stored on at least one of the one or more computer-readable tangible storage media for execution by at least one of the one or more processors via at least one of the one or more memories, wherein the computer system is capable of performing a method comprising:
    detecting at least one first finding in a medical report and at least one first candidate in a corresponding medical image;
    interpreting a geometric description of an anatomical location of the detected at least one first finding in the medical report;
    identifying, using an association algorithm, at least one true finding from the detected at least one first candidate in the corresponding medical image based on the interpreted geometric description of the anatomical location of the detected at least one finding in the medical report;

locating, in a sub-region of the corresponding medical image, the detected at least one first candidate based on the interpreted geometric description of the anatomical location of the detected at least one first finding in the medical report;

electronically marking the located at least one first candidate in the sub-region of the corresponding medical image;

generating a ground truth label by labeling, in a natural language, the electronically marked at least one first candidate in the sub-region of the corresponding medical image with the detected at least one first finding in the medical report;

training the machine learning algorithm with the generated ground truth label;

detecting, using the trained machine learning algorithm, at least one second candidate in a test medical image, wherein the at least one detected second candidate in the test medical image is associated with predicting at least one second finding from a corresponding test medical report;

generating, using the trained machine learning algorithm, a discrepancy list between the at least one detected second candidate in the test medical image and the at least one second finding in the corresponding test medical report; and in response to determining that the generated discrepancy list is above a threshold, retraining the trained machine learning algorithm until the generated discrepancy list is below the threshold.

7. The computer system of claim 6, further comprising:
determining at least one true finding from the detected at least one first candidate in the corresponding medical image, by association with the detected at least one first finding from the medical report.

8. The computer system of claim 6, further comprising:
determining a ground truth in the detected at least one first finding from the medical report; and
generating the ground truth label for the identified at least one true finding in the corresponding medical image based on the determined ground truth from the medical report.

9. The computer system of claim 8, wherein generating the ground truth label for the identified at least one true finding in the corresponding medical image further comprises:
electronically marking, using a labeling component, at least one pixel indicating a contour of the identified at least one true finding in the corresponding medical image.

10. The computer system of claim 8, wherein generating the ground truth label for the identified at least one true finding in the corresponding medical image further comprises:
providing an electronic label associated with at least one medical report data, wherein the at least one medical report data is selected from the group consisting of: at least one radiology report data and at least one pathology report data.

11. A computer program product for automatic labeling to train a machine learning algorithm, comprising:
one or more computer-readable tangible storage media and program instructions stored on at least one of the one or more computer-readable tangible storage media, the program instructions executable by a processor to cause the processor to perform a method comprising:

detecting at least one first finding in a medical report and at least one first candidate in a corresponding medical image;

interpreting a geometric description of an anatomical location of the detected at least one first finding in the medical report;

identifying, using an association algorithm, at least one true finding from the detected at least one first candidate in the corresponding medical image based on the interpreted geometric description of the anatomical location of the detected at least one finding in the medical report;

locating, in a sub-region of the corresponding medical image, the detected at least one first candidate based on the interpreted geometric description of the anatomical location of the detected at least one first finding in the medical report;

electronically marking the located at least one first candidate in the sub-region of the corresponding medical image;

generating a ground truth label by labeling, in a natural language, the electronically marked at least one first candidate in the sub-region of the corresponding medical image with the detected at least one first finding in the medical report;

training the machine learning algorithm with the generated ground truth label;

detecting, using the trained machine learning algorithm, at least one second candidate in a test medical image, wherein the at least one detected second candidate in the test medical image is associated with predicting at least one second finding from a corresponding test medical report;

generating, using the trained machine learning algorithm, a discrepancy list between the at least one detected second candidate in the test medical image and the at least one second finding in the corresponding test medical report; and in response to determining that the generated discrepancy list is above a threshold, retraining the trained machine learning algorithm until the generated discrepancy list is below the threshold.

12. The computer program product of claim 11, further comprising:
determining at least one true finding from the detected at least one first candidate in the corresponding medical image, by association with the detected at least one first finding from the medical report.

13. The computer program product of claim 11, further comprising:
determining a ground truth in the detected at least one first finding from the medical report; and
generating the ground truth label for the identified at least one true finding in the corresponding medical image based on the determined ground truth from the medical report.

14. The computer program product of claim 13, wherein generating the ground truth label for the identified at least one true finding in the corresponding medical image further comprises:
electronically marking, using a labeling component, at least one pixel indicating a contour of the identified at least one true finding in the corresponding medical image.

* * * * *